United States Patent [19]

Bryant et al.

[11] Patent Number: 5,691,355

[45] Date of Patent: *Nov. 25, 1997

[54] METHOD FOR MINIMIZING THE UTEROTROPHIC EFFECT OF TAMOXIFEN AND TAMOXIFEN ANALOGS

[75] Inventors: Henry U. Bryant, Indianapolis; Robin S. Fuchs-Young, Trafalgar, both of Ind.

[73] Assignee: Eli Lilly and Company, Indianapolis, Ind.

[*] Notice: The term of this patent shall not extend beyond the expiration date of Pat. No. 5,604,248.

[21] Appl. No.: 718,841

[22] Filed: Sep. 24, 1996

Related U.S. Application Data

[63] Continuation of Ser. No. 239,093, May 5, 1994, Pat. No. 5,604,248.

[51] Int. Cl.$^6$ ............... A61K 31/445; A61K 31/135
[52] U.S. Cl. ............................ 514/324; 514/648
[58] Field of Search ........................ 514/648, 324

[56] References Cited

U.S. PATENT DOCUMENTS

| | | | |
|---|---|---|---|
| 4,133,814 | 1/1979 | Jones et al. | 260/326.5 |
| 4,380,635 | 4/1983 | Peters | 546/202 |
| 4,418,068 | 11/1983 | Jones | 424/267 |
| 4,623,660 | 11/1986 | Richardson | 514/514 |
| 4,656,187 | 4/1987 | Black et al. | 514/324 |

OTHER PUBLICATIONS

Draper, M.W., et al., "Effects of Raloxifene (LY139481 HCl) on Biochemical Markers of Bone and Lipid Metabolism in Healthy Postmenopausal Women", Hong Kong, Fourth Int'l Symp. on Osteoporosis, Mar. 29, 1993.
Fisher, B., et al., JNCI, 86(7):527–537 (1994).
Malfetano, J.H., Gynecol. Oncol., 37:82–84 (1990).
Kirkland, J.L., et al., Molecular PHarmacology, 43:709–714 (1993).
Wakeling, A.E., et al., J. Steroid Biochem., 20(1):111–120.
Jordan, V.C., et al., Ann. N.Y. Acad. Sci. 622:439–446 (1991).
Gottardis, et al., Cancer Research, 50, 3189–3192 (1990).

Primary Examiner—Jerome D. Goldberg
Attorney, Agent, or Firm—James J. Sales; David E. Boone

[57] ABSTRACT

The present invention provides a method of minimizing the uterotrophic effect of non-steroidal antiestrogen compounds of formula II

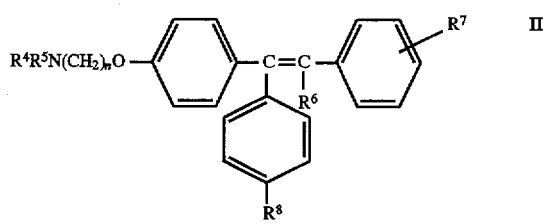

wherein
either $R^4$ is H or a lower alkyl radical and $R^5$ is a lower alkyl radical, or $R^4$ and $R^5$ are joined together with the adjacent nitrogen atom to form a heterocyclic radical;
$R^6$ is H or a lower alkyl radical;
$R^7$ is H, halo, OH, a lower alkyl radical, or is a buta-1,3-dienyl radical which together with the adjacent benzene ring forms a naphthyl radical;
$R^8$ is H or OH; and
n is 2;
or a pharmaceutically acceptable salt thereof, wherein said formula II compound is administered to a woman for the treatment or prevention of breast carcinoma, comprising concurrently or sequentially administering to said woman a compound of formula I

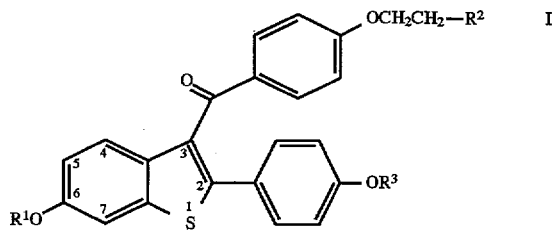

wherein $R^1$ and $R^3$ are independently hydrogen, —CH$_3$, —CO—(C$_1$–C$_6$ alkyl), or —CO—Ar, in which Ar is optionally substituted phenyl; and
$R^2$ is selected from the group consisting of pyrrolidino, hexamethyleneimino, and piperidino; or pharmaceutically acceptable salt or solvate thereof.

The present invention further provides pharmaceutical compositions comprising a compound of formula I and a compound of formula II together with a pharmaceutically acceptable carrier, excipient, or diluent.

3 Claims, No Drawings

METHOD FOR MINIMIZING THE UTEROTROPHIC EFFECT OF TAMOXIFEN AND TAMOXIFEN ANALOGS

This application is a continuation of application Ser. No. 08/239,093 filed May 5, 1994 now U.S. Pat. No. 5,604,248.

BACKGROUND OF THE INVENTION

Tamoxifen (1-p-β-dimethylaminoethoxyphenyl-trans-1, 2-diphenylbut-1-ene), represented by the structure

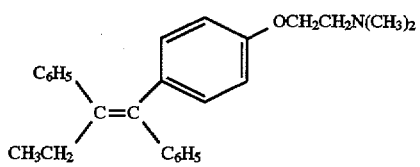

is a well known antiestrogenic compound which is useful for the treatment and prevention of mammalian breast carcinoma. See, *The Merk Index*, 11th Ed., 1430 (1989). Although tamoxifen is quite efficacious in the treatment/ prevention of this disease, it is known to induce certain uterotrophic effects which can be detrimental to the tamoxifen patient. It, therefore, would be beneficial if a pharmaceutical agent was available which would not affect the antineoplastic benefit which tamoxifen provides while minimizing or eliminating its detrimental uterotrophic effect.

Thus, the present invention provides a method of minimizing the uterotrophic effect of tamoxifen and certain tamoxifen analogs via the concurrent or sequential administration of certain known nuclear regulating benzothiophene pharmaceutical agents. Also provided are pharmaceutical compositions.

SUMMARY OF THE INVENTION

The present invention provides a method of minimizing the uterotrophic effect of non-steroidal antiestrogen compounds of formula II

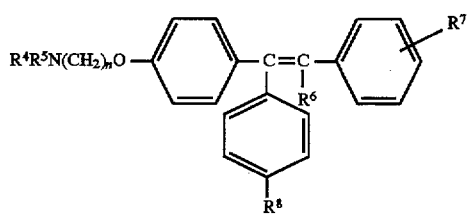

wherein either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1, 3-dienyl radical which together with the adjacent benzene ring forms a naphthyl radical;

$R^8$ is H or OH; and n is 2;

or a pharmaceutically acceptable salt thereof, wherein said formula II compound is administered to a woman for the treatment or prevention of breast carcinoma, comprising concurrently or sequentially administering to said woman a compound of formula I

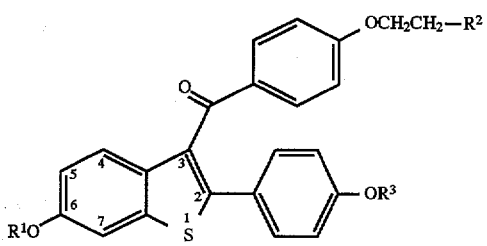

wherein $R^1$ and $R^3$ are independently hydrogen, —$CH_3$, —CO—($C_1$-$C_6$ alkyl), or —CO—Ar, in which Ar is optionally substituted phenyl; and $R^2$ is selected from the group consisting of pyrrolidino, hexamethyleneimino, and piperidino; or pharmaceutically acceptable salt or solvate thereof.

Also provided are pharmaceutical compositions comprising a compound of formula I and a compound of formula II together with a pharmaceutically acceptable carrier, excipient or diluent.

DETAILED DESCRIPTION OF THE INVENTION

The present invention concerns the discovery that a select group of 2-phenyl-3-aroylbenzothiophenes (benzothiophenes; formula I compounds) are useful for minimizing the uterotrophic effect of non-steroidal antiestrogen compounds of formula II. Formulae I and II are shown below.

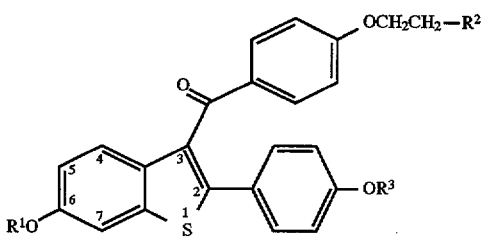

wherein $R^1$ and $R^3$ are independently hydrogen, —$CH_3$, —CO—($C_1$-$C_6$ alkyl), or —CO—Ar, in which Ar is optionally substituted phenyl; and $R^2$ is selected from the group consisting of pyrrolidino, hexamethyleneimino, and piperidino; or pharmaceutically acceptable salt or solvate thereof; and

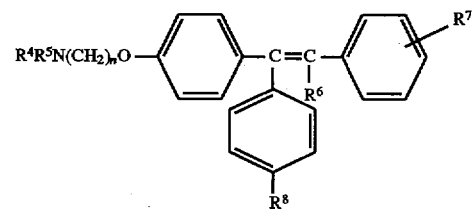

wherein either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1, 3-dienyl radical which together with the adjacent benzene ring forms a naphthyl radical;

$R^8$ is H or OH; and n is 2;

or a pharmaceutically acceptable salt thereof.

The descriptive chemical terms used with formulae I and II have their usual meaning. For example, the term "halo"

includes bromo, chloro, fluoro, and iodo. The term "lower alkyl" or "$C_1$-$C_4$ alkyl" refers to the straight and branched aliphatic radicals of 1-4 carbon atoms including methyl, ethyl, propyl, isopropyl, n-butyl, isobutyl, sec-butyl, and tert-butyl. In addition, the term "substituted phenyl" refers to a phenyl molecule having one or two substituents selected from the group consisting of $C_1$-$C_4$ alkyl, $C_1$-$C_5$ alkoxy, hydroxy, nitro, chloro, fluoro, or tri(chloro or fluoro)methyl. Finally, the term "$C_1$-$C_4$ alkoxy" includes the straight and branched aliphatic ether radicals of 1-4 carbon atoms such as methoxy, ethoxy, propoxy, isopropoxy, n-butoxy, isobutoxy, sec-butoxy, and tert-butoxy.

Raloxifene, the hydrochloride salt of a compound of formula I in which $R^1$ and $R^3$ each are hydrogen, and $R^2$ is 1-piperidinyl, is a nuclear regulatory molecule. Raloxifene has been shown to bind to estrogen receptors and originally was demonstrated to have antiestrogenic activity because it blocked the ability of estrogen to activate uterine tissue and estrogen dependent breast cancers. Indeed, raloxifene does block the action of estrogen in some cells; however in other cell types, raloxifene activates the same genes as estrogen activates and displays the same pharmacology, e.g., prevention of estrogen deficiency induced bone loss; lowering serum cholesterol. As a result, raloxifene has been referred to as a tissue selective antiestrogen with mixed agonist-antagonist properties.

Although raloxifene and estrogen generally utilize and compete for the same receptors, the pharmacological outcome of administration of the two agents is not easily predicted, and is distinct to each.

Compounds of formula I used in the methods and pharmaceutical compositions of the present invention can be made according to established procedures, such as those detailed in U.S. Pat. Nos. 4,133,814, 4,418,068, and 4,380,635, each of which is herein incorporated by reference.

Compounds of formula I form pharmaceutically acceptable acid and base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzene-sulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts and solvates generally have enhanced solubility characteristics compared to the compound from which they are derived, and thus are often more amenable to formulation as liquids or emulsions.

Compounds of formula II used in the methods and pharmaceutical compositions of the present invention are prepared by established procedures, such as those described in U.S. Pat. No. 4,623,600, which is herein incorporated by reference. Pharmaceutically acceptable acid addition salts of formula II compounds are prepared via the above-described process.

A preferred formula II compound, in which $R^4$ and $R^5$ each are methyl, $R^6$ is ethyl, $R^7$ and $R^8$ each are H, and n is 2, is known in the art as tamoxifen. Tamoxifen and its formula II analogs are antiestrogen compounds and tamoxifen primarily is used for the treatment of breast carcinoma in women. In addition to this well known activity, it also is well recognized in the art that tamoxifen may cause certain side-effects, particularly endometrial cancer, which potentially could be life threatening [see, e.g., Fisher, B., et al., JNCI, 86(7):527-537 (1994)].

One aspect of the present invention provides a method of minimizing the uterotrophic effect of a non-steroidal antiestrogen compound of formula II, particularly tamoxifen, by administering a compound of formula I, particularly raloxifene, to a woman receiving administrations of a formula II compound for the treatment or prevention of breast carcinoma. In this context, "uterotrophic effect" means the proliferation of uterine epithelial cells, which frequently can be a side effect of tamoxifen administration to women. It appears as if this uterotrophic effect is directly involved with endometrial cancer.

Administration of a formula I compound, particularly raloxifene, minimizes the uterotrophic effect of a concurrently or sequentially administered formula I compound, particularly, tamoxifen, without affecting the formula II compounds efficacy against breast carcinoma. The term "minimize", or a derivative thereof, includes partial or complete inhibition of the tamoxifen-induced uterotrophic effect on uterine epithelial cells.

For the treatment of human breast carcinoma, tamoxifen can be administered alone or in combination with other chemotherapeutic agents and/or radiotherapy, as an adjuvant to surgery, or, in certain circumstances, may be considered for use as a chemosuppressive/chemoprophylactic agent. Because each of these administration regimes may present various degrees of risk of uterotrophic side effects, the attending physician is best suited to decide whether the administration of a formula I compound should be concurrent or sequential to the administration of a formula II compound.

When administered sequentially, pharmaceutical formulations of compounds of formulae I and II are prepared by methods known by one of ordinary skill in the art.

When administered concurrently, formula I and formula II compounds may be prepared into pharmaceutical formulations via the above-mentioned known methods, and administered as separate entities. Alternatively, they may be combined to form a pharmaceutical composition of the present invention which comprises an effective amount of a formula I compound and an effective amount of formula II compound, preferably raloxifene and tamoxifen, respectively, together with a pharmaceutically acceptable carrier, excipient, or diluent.

As used above and throughout this specification, the term "effective amount" means that dosage of active compound (s) sufficient to provide therapeutic treatment of the specified medical indication.

The term "active compound" as used throughout this specification, refers to a formula I compound, or a pharmaceutically acceptable salt or solvate thereof, and/or a formula II compound, or a pharmaceutically acceptable salt thereof.

For therapeutic treatment of the specified indications, a formula I compound, with or without a formula II compound, may be administered as such, or can be compounded and formulated into pharmaceutical compositions in unit dosage form for parenteral, transdermal, rectal, nasal, intravenous administration or, preferably, oral administration. Such pharmaceutical compositions are prepared in a manner well known in the art and comprise a formula I compound, optionally including a compound of formula II. In making the compositions of the present invention, the active ingredients will usually be mixed with a carrier, or diluted by a carrier, or enclosed within a carrier which may be in the form of a capsule, sachet, paper or other container. When the carrier serves as a diluent, it may be a solid, semisolid, or liquid material which acts as a vehicle, excipient or medium for the active ingredient. Thus, the composition can be in the form of tablets, pills, powders, lozenges, sachets, cachets, elixirs, emulsions, solutions, syrups, suspensions, soft and hard gelatin capsules, sterile injectable solutions, and sterile packaged powders.

Additionally, compounds of the present composition, particularly formula I compounds, are well suited to formulation as sustained release dosage forms and the like. The formulations can be so construed that they release the active ingredient only or preferably in a particular physiological location, possibly over a period of time. The coatings, envelopes, and protective matrices may be made, for example, from polymeric substances or waxes.

Some examples of suitable carriers, excipients, and diluents include lactose, dextrose, sucrose, sorbitol, mannitol, starches, gum acacia, calcium phosphate alginates, calcium salicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The compositions can additionally include lubricating agents, wetting agents, emulsifying and suspending agents, preserving agents, sweetening agents or flavoring agents. The compositions may be formulated so as to provide quick, sustained, or delayed release of the active ingredient(s) after administration to the patient by employing procedures well known in the art. For oral administration, a compound optionally including a second component compound, can be admixed with carriers and diluents molded into tablets or enclosed in gelatin capsules. The mixtures can alternatively be dissolved in liquids such as 10% aqueous glucose solution, isotonic saline, sterile water, or the like, and administered intravenously or by injection.

The compositions are preferably formulated in a unit dosage form, each dosage containing from about 1 to about 500 mg and, more frequently, from about 5 to about 300 mg of the active ingredient(s). The term "unit dosage form" refers to physically discreet units suitable as unitary dosages for human subjects, each unit containing a predetermined quantity of active ingredients calculated to produce the desired therapeutic effect, in association with the required pharmaceutically acceptable carrier. By "pharmaceutically acceptable", it is meant the carrier, diluent, or excipient must be acceptable with the other ingredients of the formulation and not deleterious to the recipient thereof.

Compounds of formula I, alone or in combination with a pharmaceutical agent of the present invention, generally will be administered in a convenient formulation. The following formulation examples only are illustrative and are not intended to limit the scope of the present invention.

FORMULATIONS

Formulation 1

Gelatin Capsules

Hard gelatin capsules are prepared using the following:

| Ingredient | Quantity (mg/capsule) |
| --- | --- |
| Formula I compound | 0.1–1000 |
| Starch, NF | 0–650 |
| Starch flowable powder | 0–650 |
| Silicone fluid 350 centistokes | 0–15 |

Formulation 2

Raloxifene capsule

| Ingredient | Quantity (mg/capsule) |
| --- | --- |
| Raloxifene HCl | 1 |
| Starch, NF | 112 |
| Starch flowable powder | 225.3 |
| Silicone fluid 350 centistokes | 1.7 |

Formulation 3

Raloxifene capsule

| Ingredient | Quantity (mg/capsule) |
| --- | --- |
| Raloxifene HCl | 5 |
| Starch, NF | 108 |
| Starch flowable powder | 225.3 |
| Silicone fluid 350 centistokes | 1.7 |

Formulation 4

Raloxifene capsule

| Ingredient | Quantity (mg/capsule) |
| --- | --- |
| Raloxifene HCl | 10 |
| Starch, NF | 103 |
| Starch flowable powder | 225.3 |
| Silicone fluid 350 centistokes | 1.7 |

Formulation 5

Raloxifene capsule

| Ingredient | Quantity (mg/capsule) |
|---|---|
| Raloxifene HCl | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6

Tablets

| Ingredient | Quantity (mg/tablet) |
|---|---|
| Formula I compound | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 25–1000 mg of a formula I compound are made up as follows:

Formulation 7

Tablets

| Ingredient | Quantity (mg/tablet) |
|---|---|
| Formula I compound | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The formula I compound, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 500°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 25–1000 mg of medicament per 5 ml dose are made as follows:

Formulation 8

Suspensions

| Ingredient | Quantity (mg/5 ml) |
|---|---|
| Formula I compound | 25–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Formulation 9

Raloxifene and Tamoxifen Capsule

| Ingredient | Quantity (mg/capsule) |
|---|---|
| Raloxifene HCl | 200 |
| Tamoxifen | 20 |
| Avicel pH 101 | 50 |
| Starch 1500 | 117.50 |
| Silicon Oil | 2 |
| Tween 80 | 0.50 |
| Cab-O-Sil | 0.25 |

Formulation 10

Raloxifene and Tamoxifen Capsule

| Ingredient | Quantity (mg/capsule) |
|---|---|
| Raloxifene HCl | 200 |
| Tamoxifen | 20 |
| Avicel pH 101 | 82.50 |
| Starch 1500 | 90 |
| Silicon Oil | 2 |
| Tween 80 | 0.50 |

Formulation 11

Raloxifene and Tamoxifen Tablet

| Ingredient | Quantity (mg/capsule) |
|---|---|
| Raloxifene HCl | 200 |
| Tamoxifen | 20 |
| Corn Starch NF | 50 |
| Povidone, K29–32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The particular dosage of a compound of formula I, particularly Raloxifene, required to minimize the uterotrophic effect of a non-steroidal antiestrogen compound of formula II according to this invention will depend upon the severity of the condition, the route of administration, and related factors that will be decided by the attending physician. Generally, accepted and effective daily doses of a formula I compound will be from about 0.1 mg to about 1000 mg/day, and more typically from about 50 mg to about 600 mg/day. Such dosages will be administered to a subject in need of treatment from once to about three times each day, or more often as needed to effectively treat the present indication. Usually, it is preferred to administer a compound of formula I in the form of an acid addition salt, as is customary in the administration of pharmaceuticals bearing a basic group, such as a piperidino ring. It also is advantageous to administer such as a compound by the oral route.

Compounds of formula II, particularly tamoxifen, are administered for the treatment of breast carcinoma at dosages and timings which are consistent with those which are well known in the art. However, it is preferred to administer a substantial excess of a formula I compound relative to a formula II compound.

Test Procedure

General Preparation Procedure

In the examples illustrating the methods, a post-menopausal-type model was used in which the uterine response of different treatments was determined.

Seventy-five day old female Sprague Dawley rats (weight range of 200 to 250 g) were obtained from Charles River Laboratories (Portage, Mich.). The animals were bilaterally ovariectomized (OVX) at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2° ±1.7° C. with a minimum relative humidity of 40%. The photoperiod in the room was 12 hours light and 12 hours dark.

Dosing Regimen Tissue Collection.

After a one week acclimation period (therefore, two weks post-OVX) daily dosing with test compound was initiated. The test compounds were given subcutaneously as a suspension in 1.5% carboxymethylcellulose. Animals were dosed daily for 4 days. Following the dosing regimen, animals were weighed and anesthetized with a ketamine: Xylazine (2:1, V:V) mixture and a blood sample was collected by cardiac puncture. The animals were then sacrificed by asphyxiation with $CO_2$, the uterus was removed through a midline incision, and a wet uterine weight was determined.

Antagonism of Tamoxifen Stimulation of Rat Uteri by Raloxifene

Data presented in Table 1 below show comparative results among ovariectomized rats, rats treated with 0.01, 0.1, and 1.0 mg/kg of tamoxifen, and rats treated with the same doses of tamoxifen plus 10 mg/kg of raloxifene.

TABLE 1

| Treatment | Dose (mg/kg) | Uterine Weight (mg) |
| --- | --- | --- |
| Ovariectomy | — | 117.7 ± 3.3 |
| Tamoxifen | 0.01 | 151.8 ± 15.2 |
|  | 0.1 | 194.8 ± 6.7 |
|  | 1.0 | 204.8 ± 11.2 |
| Tamoxifen + Raloxifene | 0.01 + 10.0 | 140.6 ± 6.5 |
|  | 0.1 + 10.0 | 151.2 ± 1.1 |
|  | 1.0 + 10.0 | 164.6 ± 7.4 |

These data demonstrate that raloxifene, administered at a dose of 10 mg/kg with tamoxifen, significantly antagonizes the uterine stimulatory effect of tamoxifen, particularly when administered with higher therapeutic doses of tamoxifen.

I claim:

1. A pharmaceutical composition comprising an effective amount of a first component which is a compound of formula II

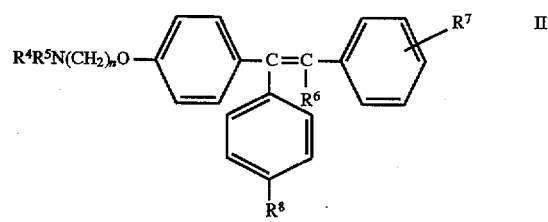

wherein either $R^4$ is H or a lower alkyl radical and $R^5$ is a lower alkyl radical, or $R^4$ and $R^5$ are joined together with the adjacent nitrogen atom to form a heterocyclic radical;

$R^6$ is H or a lower alkyl radical;

$R^7$ is H, halo, OH, a lower alkyl radical, or is a buta-1, 3-dienyl radical which together with the adjacent benzene ring forms a naphthyl radical;

$R^8$ is H or OH; and n is 2;

or a pharmaceutically acceptable salt thereof, and an effective amount of a second component, for minimizing the uterotrophic effect of said formula II compound, which is a compound of formula I

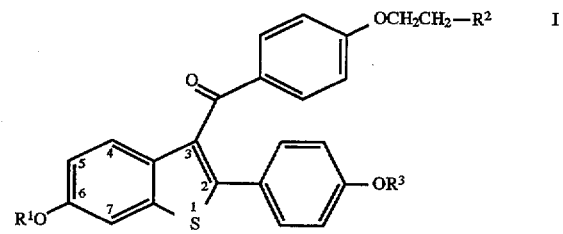

wherein $R^1$ and $R^3$ each are hydrogen; and $R^2$ is piperidino;

or a pharmaceutically acceptable salt or solvate thereof, together with a pharmaceutically acceptable carrier, excipient or diluent.

2. A pharmaceutical composition according to claim 1 wherein $R^4$ and $R^5$ each are methyl;

$R^6$ is ethyl;

$R^7$ is H;

$R^8$ is H; and n is 2;

or a pharmaceutically acceptable salt thereof.

3. A pharmaceutical composition according to claim 2 wherein said formula I compound is the hydrocholoride salt thereof.

* * * * *